(12) United States Patent
Kelley et al.

(10) Patent No.: US 8,087,309 B2
(45) Date of Patent: Jan. 3, 2012

(54) HERMETIC SAMPLE HOLDER AND METHOD FOR PERFORMING MICROANALYSIS UNDER CONTROLLED ATMOSPHERE ENVIRONMENT

(75) Inventors: Tracy Earl Kelley, Tucson, AZ (US); John D. May, Marana, AZ (US); Vladimir Oleshko, Tucson, AZ (US); Chariclea Scordilis-Kelley, Tucson, AZ (US)

(73) Assignee: Sion Power Corporation, Tucson, AZ (US)

( * ) Notice: Subject to any disclaimer, the term of this patent is extended or adjusted under 35 U.S.C. 154(b) by 280 days.

(21) Appl. No.: 12/471,095

(22) Filed: May 22, 2009

(65) Prior Publication Data
US 2010/0294049 A1 Nov. 25, 2010

(51) Int. Cl.
*G01N 1/00* (2006.01)
(52) U.S. Cl. ...................................... 73/864.81; 220/820
(58) Field of Classification Search .......................... None
See application file for complete search history.

(56) References Cited

U.S. PATENT DOCUMENTS 2,292,087 A * 8/1942 Ramo ....................... 250/441.11
3,886,358 A * 5/1975 McLaughlin et al. ......... 250/289

FOREIGN PATENT DOCUMENTS
WO WO 02/45125 A1 6/2002

OTHER PUBLICATIONS

P D P Koch and H B Wild, Airtight Cover for Specimem Stubs for the Scanning Electron Microscope, Journal of Scientific Instruments (Journal of Physics E), 1969, pp. 451-452, Series 2, vol. 2, The Institute of Physics and the Physical Society, London England.
J. Steger and J. Alonzo, Vacuum-sealed Specimem Stage for Scanning Microscopy of Air-sensitive Materials, Rev. Sci. Instrum., Jan. 1979, pp. 130-131, vol. 50, No. 1, American Institute of Physics.

* cited by examiner

*Primary Examiner* — Robert Raevis
(74) *Attorney, Agent, or Firm* — Wolf, Greenfield & Sacks, P.C.

(57) ABSTRACT

A hermetic sample holder for use in performing microanalysis of a sample under a controlled atmosphere environment. The sample holder comprises a sample holder body with a sample cavity to receive the sample and a cover movably mounted to the holder body between an open position to allow access to the cavity and a closed position to seal the cavity. The cover is secured in and released from the closed position at least in part by a pressure differential between the cavity and the ambient atmosphere. The cover may be biased toward the open position. The cover may be pivotally mounted about an axis that is perpendicular to a sealing surface of the cover and/or movable in a direction along the pivot axis. A valve may be provided to allow direct evacuation of the cavity to create a pressure differential. An adjustable clamp may be located in the cavity to secure the sample.

15 Claims, 6 Drawing Sheets

HERMETIC SAMPLE HOLDER AND METHOD FOR PERFORMING MICROANALYSIS UNDER CONTROLLED ATMOSPHERE ENVIRONMENT

BACKGROUND

1. Field

The present disclosure relates to a sample holder and method for performing analysis of a material, such as microstructural and elemental analyses of a material under a controlled atmosphere environment.

2. Discussion of Related Art

Various analyses, including microstructural and elemental analyses, are conducted on material using different types of analysis equipment and techniques, such as a scanning electron microscope (SEM), X-ray photoelectron spectroscopy (XPS), and Auger analysis. In microanalysis, most instruments operate under vacuum, and the material sample may be prepared in a controlled atmosphere, such as an argon-filled glove box, before being placed in the sample chamber of the analysis equipment.

It may be desirable to analyze the material without exposure to air or an ambient environment that could potentially contaminate the material. Such exposure, even briefly, could potentially alter a sample in a way that leads to inaccurate or misleading results. For example, it may be desirable to avoid absorption of or reaction with water and other components of ambient air, such as oxygen, carbon dioxide, nitrogen, and the like, that could give rise to severe artifacts. Such a chemical reaction or physical absorption could lead to morphological and compositional changes of the sample and subsequently to loss of desirable functional properties of related materials and devices.

Transferring the material sample from the controlled atmosphere environment to the sample chamber of the equipment could lead to potential contamination of the sample due to exposure to the ambient atmosphere during the material transfer.

It is an object to provide a sample holder for reducing the potential contamination of a material sample that is to be subjected to microstructural and elemental analyses in a controlled atmosphere environment.

SUMMARY

In one illustrative embodiment, a hermetic sample holder is provided for use in performing microanalysis of a sample. The sample holder comprises a sample holder body with a sample cavity to receive the sample that is to be subjected to microanalysis, and a cover movably mounted to the sample holder body. The cover is movable between an open position to allow access to the sample cavity and a closed position to hermetically seal the sample cavity. The cover is to be secured in the closed position and released from the closed position at least in part by a pressure differential between an internal pressure within the sample cavity and an ambient pressure outside the sample cavity.

According to one aspect, the cover is biased toward the open position.

According to another aspect, the cover includes a sealing surface that cooperates with the sample holder body to seal the sample cavity. The cover is pivotally mounted to the sample holder body about a pivot axis that is perpendicular to the sealing surface.

According to a further aspect, the sample holder further comprises a valve in fluid communication with the sample cavity to allow direct evacuation of the sample cavity to create a pressure differential between the sample cavity and the ambient pressure.

According to another aspect, the sample holder further comprises an adjustable clamp located in the sample cavity to secure the sample.

According to a further aspect, the cover is pivotally mounted to the sample holder body about an axis to pivot between the open and closed positions, and the cover is movable in a direction along the axis toward and away from the sample holder body.

According to another aspect, the sample holder further comprises an interlock between the cover and the sample holder body to secure the cover in the closed position. The interlock is configured to secure and release the cover based on the differential pressure between the internal and ambient pressures.

In another illustrative embodiment, a method is provided of transporting a sample for microanalysis. The method comprises acts of placing the sample in a sample cavity of a sample holder within a controlled atmosphere environment; hermetically sealing the sample cavity with a cover by reducing the pressure of the sample cavity to a first pressure that is less than the ambient pressure of the controlled atmosphere environment; transporting the sample holder from the controlled atmosphere environment to an analyzer chamber; and releasing the cover to expose the sample to the atmosphere of the analyzer chamber by reducing the pressure of the analyzer chamber relative to the first pressure of the sample cavity.

According to one aspect, the pressure of the sample cavity is reduced by directly evacuating the sample cavity independent of adjusting the ambient pressure of the controlled atmosphere environment.

According to another aspect, the cover is released by applying a separate biasing force to the cover.

According to a further aspect, the method further comprises an act of securing the cover with an interlock that locks and releases the cover based on the pressure differential between the sample cavity and the ambient atmosphere.

BRIEF DESCRIPTION OF DRAWINGS

Various embodiments will now be described, by way of example, with reference to the accompanying drawings, in which.

DETAILED DESCRIPTION

It should be understood that aspects of the invention are described herein with reference to the figures, which show illustrative embodiments in accordance with aspects of the invention. The illustrative embodiments described herein are not necessarily intended to show all aspects of the invention, but rather are used to describe one or more illustrative embodiments. Thus, aspects of the invention are not intended to be construed narrowly in view of the illustrative embodiments. In addition, it should be understood that aspects of the invention may be used alone or in any suitable combination with other aspects of the invention.

The present invention is directed to a sample holder that may be used in performing various analyses, including microstructural and elemental analyses of a material. The holder is particularly suited for transporting a sample of material, such as biological and non-biological materials, from a controlled atmosphere environment, such as a glove box, to the chamber of an instrument, such as a scanning electron microscope (SEM), for analyzing the material. The holder may be configured to maintain a desired atmosphere for the sample and protect the sample from the ambient atmosphere during transport to the instrument chamber. In this manner, it may be possible to reduce or avoid potential contamination of the sample with moisture and/or other components of ambient air, such as oxygen, carbon dioxide, nitrogen and the like.

The sample holder may be configured to hold and hermetically seal the sample within a desired atmosphere during its transport to the instrument chamber. For example, the sample may be prepared in a controlled atmosphere environment, such as an argon-filled glove box maintained below 10 ppm (parts per million) water and oxygen. The sample may then be sealed within a chamber or cavity of the holder. Some of the glove box atmosphere may also become sealed in the holder. If desired, the sample may be sealed in the holder with any other desired gas or atmosphere that may be introduced and maintained in the holder.

After transport to the instrument chamber, the sample holder may be opened to expose the sample for analysis. In one aspect of the invention, the sample holder is configured to be sealed and opened in response to a pressure differential between the holder cavity and the external atmosphere. In this manner, the holder is configured to automatically open when a predetermined pressure differential exists between the sample cavity and external atmosphere. This arrangement may be particularly suited for use with instruments, such as an SEM, that operate under a vacuum to analyze samples within a sealed chamber of the device.

In one embodiment, the sample holder is configured to seal the sample when the external pressure of the ambient atmosphere is greater than the internal pressure of the atmosphere within the chamber or cavity of the holder. Conversely, the sample holder is configured to open and expose the sample when the external pressure of the ambient atmosphere is less than the internal pressure of the holder.

According to one aspect, the sample holder may include a sample holder body with a chamber or cavity that receives and holds the sample. A cover may be movably mounted to the holder body between an open position to allow access to the cavity and a closed position to seal the cavity. In one embodiment, the cover is sealed closed or opens based on a predetermined pressure differential between the holder cavity atmosphere and the external ambient atmosphere.

According to one aspect, the cover may be pivotally mounted to the sample holder body so that the cover rotates or pivots about a pivot axis between the open and closed positions. In one embodiment, the cover pivots about an axis that is perpendicular to a sealing surface of the cover. In this manner, the cover pivots in a plane parallel to the sealing surface so that the cover may be opened and closed with minimal clearance requirements between the sample holder and the instrument.

According to one aspect, the cover may be biased toward the open position to facilitate opening the holder. In one embodiment, a spring may be employed to bias the cover toward the open position.

According to one aspect, the cover may also be movable relative to the sample holder body in a direction that is substantially parallel to the pivot axis. In this manner, the sealing surface may move toward or away from the holder body to facilitate closing and opening of the cover by allowing the sealing surface to raise away from the holder body. This may be particularly suited for use with an SEM equipped with an intermediate airlock or antechamber under vacuum to transfer a sample into the main SEM chamber.

A seal may be provided to facilitate the formation of a hermetic seal within the sample cavity. The seal may be located between the cover and the holder body so as to engage the sealing surface of the cover when the cover is closed against the holder body. In one embodiment, the seal may include an o-ring that extends about an access opening to the sample cavity and becomes compressed between the cover and the body to seal the sample cavity.

According to one aspect, an interlock may be provided to secure the cover in the closed position on the sample body holder. In this manner, the interlock may be configured to resist a biasing force being applied to open the cover. The interlock may be configured to secure and release the cover based on the pressure differential between the cavity and ambient atmospheres.

The interlock may include corresponding locking features that engage with and disengage from each other in response to movement of the cover toward or away from the holder body in the direction along the pivot axis. In one embodiment, the interlock may include a pin that protrudes from the cover and cooperates with a corresponding feature, such as a hole, provided on the holder body. The pin may be oriented in a direction that is parallel to the pivot axis. Alternatively, the hole may be provided on the cover with the pin protruding from the holder body.

According to one aspect, the sample holder may be configured to allow direct evacuation of the sample chamber or cavity to create a vacuum within the cavity that seals and locks the cover to the body. The sample holder may include a valve that is in fluid communication with the sample cavity. In one embodiment, the sample holder employs a syringe valve that can be opened and closed to either permit or prevent fluid passage to and from the sample cavity. The sample cavity may be evacuated to create a vacuum therein by drawing fluid from the sample cavity through the valve using a syringe. Such an arrangement allows a user to control the amount of vacuum created within the cavity.

According to one aspect, the sample holder may include an adjustable clamp for securing a sample within the sample cavity. The clamp may include one or more plates that are slidably mounted within the sample cavity. One or more an adjustment features may be provided to adjust and maintain the clamp in a desired position to secure the sample.

In one illustrative embodiment shown in FIGS. 1-4, a hermetic sample holder 20 includes a sample holder body 22 and a cover 24. The sample holder body has a chamber or cavity 26 that receives and holds a sample. The cover 24 is movably mounted to the holder body 22 between an open position to allow access to the cavity and a closed position to seal the cavity.

The cover 24 may be pivotally mounted to the sample holder body 22 so that the cover rotates or pivots about a pivot axis 28 between the open (FIGS. 1-3) and closed (FIG. 4) positions. In one illustrative embodiment, the cover 24 pivots about an axis 28 that is perpendicular to a sealing surface 30 of the cover. This arrangement allows the cover to open and close in a generally fixed plane relative to the holder body. Such an arrangement may be desirable for use with instruments that have limited vertical space between the sample holder and the instrumentation.

In one illustrative embodiment, the sample holder 20 is sealed in the closed position based on a predetermined pressure differential between the atmosphere of the holder cavity and the external ambient atmosphere. More particularly, when the cover 24 is placed in its closed position over the cavity 26 and the pressure within the cavity is lowered a predetermined amount below the ambient atmosphere (a negative pressure differential), the cover 24 will be drawn into sealing engagement against the holder body 22 to seal the holder.

In a similar manner, the sample holder 20 is configured to open and expose the sample contained in the cavity 26 based on a predetermined pressure differential between the cavity and the ambient atmosphere. More particularly, when the external ambient pressure is lowered a predetermined amount below the cavity pressure (a positive pressure differential), the cover 24 will release from its sealing engagement with the holder body 22 so that the cover can open to expose the cavity 26 and the sample therein. It is also to be appreciated that a positive pressure differential may not be necessary for the cover to open as the cover may be released and open as the pressure differential approaches zero.

To facilitate opening the sample holder, the cover 24 may be biased toward the open position. In this manner, the cover will automatically open when the differential pressure between the cavity 26 and ambient atmosphere releases the cover 24 from sealing engagement with the sample holder body 22.

In one illustrative embodiment, the sample holder 20 includes a spring 31, such as a torsion spring, that is located about the pivot axis 28 and between the cover 24 and the holder body 22. The spring 31 is coupled to the cover and the holder body so that the spring becomes loaded when the cover is rotated to its closed position. This generates a biasing force on the cover which will open the cover when it releases from the holder body in response to the pressure differential between the cavity and the external atmosphere.

In one illustrative embodiment, the sample holder employs a torsion spring that is rated at 0.117 in-lbs of torque. One example of a suitable torsion spring is McMaster part no. 9287K11. It is to be appreciated that other biasing arrangements, if desired, may be employed with the sample holder as would be apparent to one of skill in the art.

For some arrangements, it may be desirable to restrict or limit the rotation or pivoting of the cover. For example, restricting the amount and/or direction of cover rotation may help avoid over-stressing a spring, such as a torsion spring, that may be employed to bias the cover to the open position.

Figure 2:
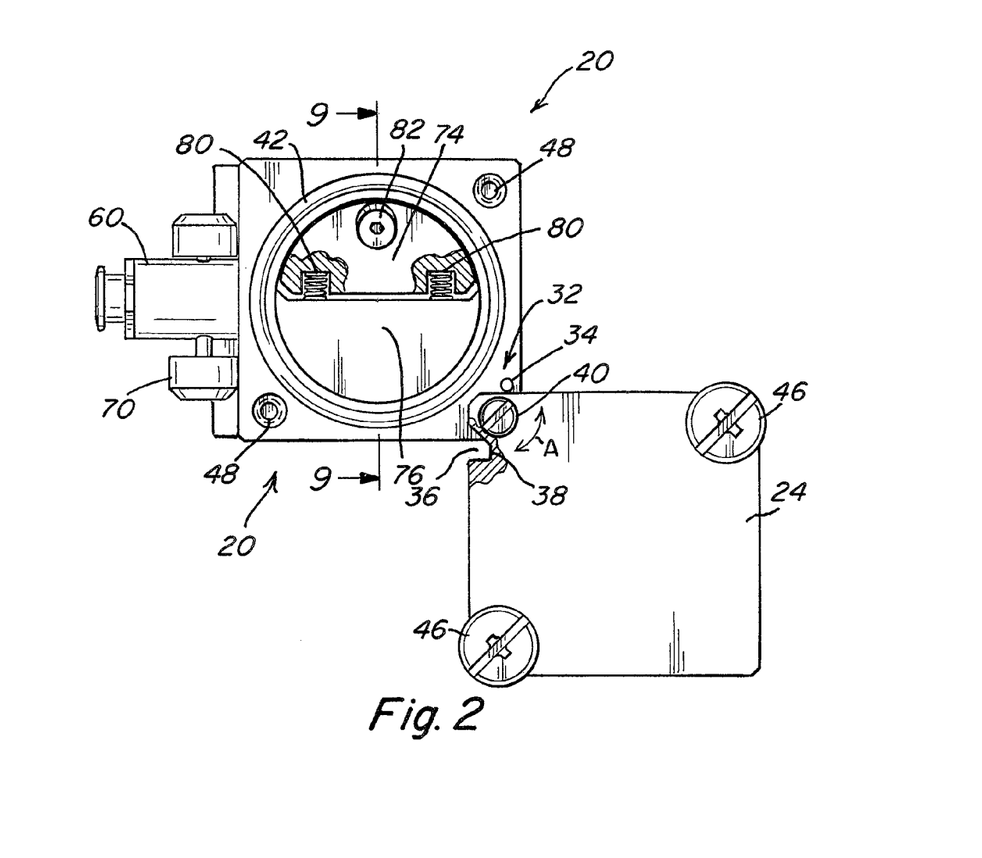
FIG. 2 is a top plan view of the hermetic sample holder of FIG. 1.
Figure 3:
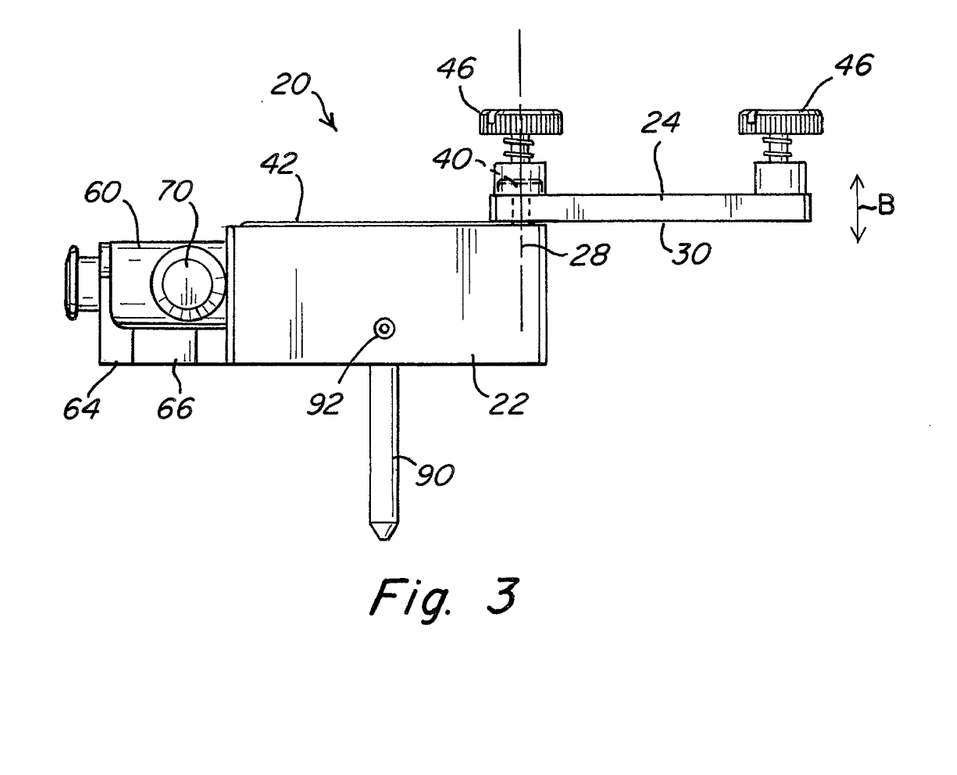
FIG. 3 is a side elevation view of the hermetic sample holder of FIG. 1.

The sample holder 20 may include a restrictor 32 that is configured to restrict or limit the amount of cover rotation relative to the sample body. The restrictor may also be configured to restrict the direction of rotation. In one illustrative embodiment shown in FIGS. 2 and 5, the restrictor 32 may include an upstanding pin 34 on the sample body 22 that is received within a recess 36 in the bottom surface of the cover 24 when the cover is rotated to the closed position. The recess 36 may have a closed end 38 defined by a portion of the cover that engages with the pin 34 to restrict rotation of the cover in the clockwise direction (when viewed from the top). In this manner, the closed end acts as a stop to limit the cover rotation when engaged by the pin. As shown in FIG. 2, the pin is arranged to engage the outer edge of the cover 24 to limit the cover rotation in the counter-clockwise direction. As shown, the restrictor may be located adjacent the pivot axis of the cover. It is to be appreciated that other restrictor arrangements, if desired, may be employed with the sample holder as would be apparent to one of skill in the art.

The cover 24 may also be movable relative to the sample holder body 22 in a direction that is substantially parallel to the pivot axis 28. In this manner, the sealing surface 30 may move toward or away from the holder body to facilitate closing and opening of the cover.

In one illustrative embodiment shown in FIGS. 1-5, the cover 24 is mounted to the holder body 22 with a fastener 40 that allows the cover to both pivot (FIGS. 1-2, direction A) about the fastener 40 and move (FIG. 1, direction B) along the axis 28 of the fastener. The cover 24 may be mounted to the holder body 22 using a shoulder screw having a shoulder length that is greater than the thickness of the cover so that the cover can move along the length of the shoulder. In one embodiment, the shoulder screw has a shoulder length of approximately 0.125 inches and the cover has a thickness of approximately 0.120 inches to allow the cover to travel approximately 0.005 inches along the length of the shoulder. However, it is to be appreciated that other suitable arrangements may be employed to fasten the cover to the holder body as would be apparent to one of skill in the art.

The sample holder 20 may include a seal 42 to facilitate the formation of a hermetic seal within the sample cavity. The seal may be located between the cover and the holder body so as to engage the sealing surface of the cover when the cover is closed against the holder body.

Figure 1:
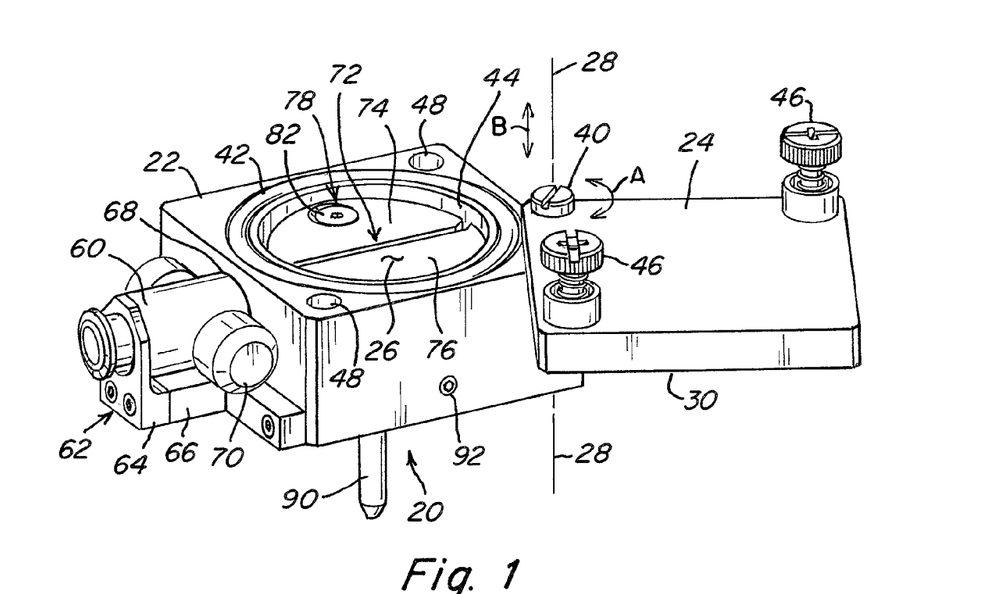
FIG. 1 is a perspective view of the hermetic sample holder in an open configuration according to one illustrative embodiment.

In one illustrative embodiment shown in FIGS. 1-2, the seal 42 includes an o-ring that extends about an access opening 44 to the sample cavity 26. The o-ring becomes compressed between the cover and the body to seal the sample cavity as the cover is drawn against the holder body in response to the creation of a negative differential pressure between the cavity and the external atmosphere.

In one embodiment, the seal 42 may include an o-ring of Buna-N material having a durometer of Shore A 50. One example of a suitable o-ring is McMaster part no. 2418T128. It is to be appreciated that other suitable seal arrangements may be employed with the sample holder as would be apparent to one of skill in the art.

It may be desirable to provide the sample holder with a locking arrangement for temporarily securing the cover in the closed position until a pressure differential that is sufficient to seal the cover to the holder body is formed between the cavity and external atmosphere. In one illustrative embodiment as shown in FIGS. 1-4, the sample holder 20 includes at least one fastener 46 that can be tightened to secure the cover in the closed position. As shown, the sample holder may include a pair of captive screws 46 that are mounted to the cover 24 and which engage a corresponding pair of threaded holes 48 provided in the holder body 22.

With the cover in its closed position (FIG. 4), the screws 46 may be tightened to draw the cover 24 against and compress the seal 42. After a differential pressure is created within the holder to seal the cover, the screws may be loosened so that the cover can then automatically open in response to a change in the differential pressure between the sample cavity and the ambient atmosphere around the holder. In this regard, a rise in the pressure within the cavity relative to the ambient pressure will allow the seal 42 to decompress, which in turn will raise the cover 24 away from the holder body 22 to a point where the biasing force of the spring 31 will swing the cover to the open position.

If it is desirable to reduce the height of the holder, the fasteners 46 may include screws, such as thumb screws, that can be removed from the holder after the cover is sealed to the holder body.

Rather than or in addition to fasteners for temporarily securing the cover, the sample holder 20 may include an interlock to aid in securing the cover in the closed position on the sample body holder. The interlock may be configured to resist a biasing force, such as generated by the torsion spring, being applied to open the cover. The interlock may be configured to automatically secure and release the cover based on the pressure differential between the cavity and ambient atmospheres. The interlock may include corresponding locking features that engage with and disengage from each other in response to movement of the cover toward or away from the holder body in the direction along the pivot axis.

Figures 5, 6:
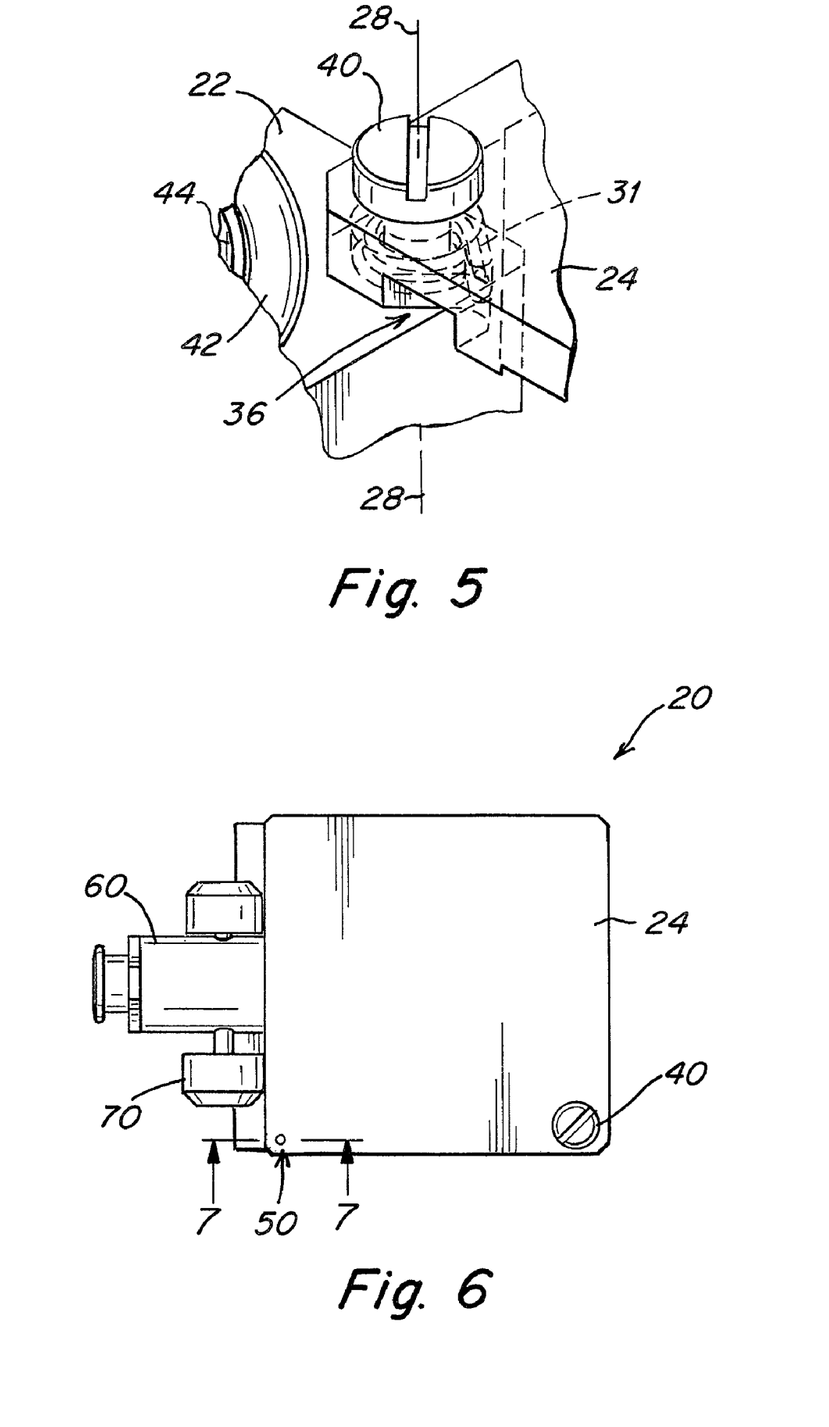
FIG. 5 is an enlarged perspective view of a pivotal mounting arrangement between the sample holder body and the cover according to one illustrative embodiment with the cover shown in phantom to illustrate the mounting arrangement.
FIG. 6 is a top plan view of the hermetic sample holder according to another illustrative embodiment.
Figure 7A:
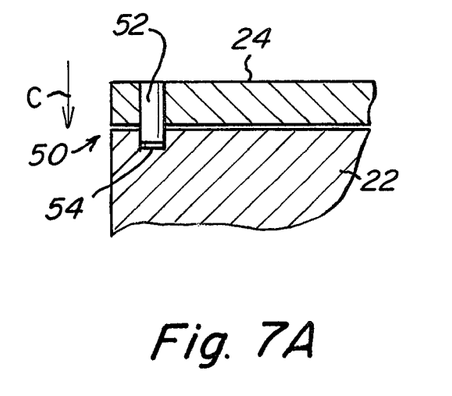
FIGS. 7A-7B are cross sectional views taken along section line 7-7 of FIG. 6 showing an interlock between the cover and the sample body according to one illustrative embodiment.
Figure 7B:
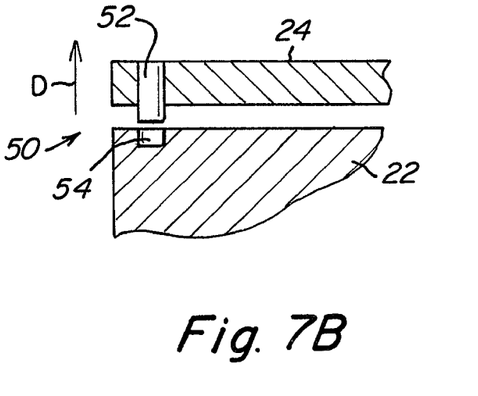

In one illustrative embodiment shown in FIGS. 6-7B, the interlock 50 may include a pin 52 that protrudes from the cover 24 and cooperates with a corresponding hole 54 provided on the holder body 22. Alternatively, the hole may be provided on the cover with the pin protruding from the holder body. The pin may be oriented in a direction that is parallel to the pivot axis.

As the pressure within the cavity 26 is lowered relative to the external atmosphere, the cover 24 is drawn toward (FIG. 7A, direction C) the holder body 22 and the pin 52 engages the hole 54 to provide a direct mechanical interlock between the cover and body that prevents the cover from swinging open despite the biasing force being exerted to open the cover. Conversely, as the pressure within the cavity increases relative to the external pressure, the cover 24 will rise away (FIG. 7B, direction D) from the holder body 22 due to decompression of the seal 42 so that the pin 52 disengages from the hole 54. The cover can then swing open due to the biasing force exerted on the cover by the spring.

The sample holder may be configured to allow direct evacuation of the sample cavity to create a vacuum within the cavity that seals and locks the cover to the body. In one illustrative embodiment shown in FIGS. 1-4, the sample holder 20 includes a valve 60 that is in fluid communication with the sample cavity 26. As shown, the valve 60 may be mounted to a side of the holder body 22 with a mounting bracket 62 that may include one or more plates 64, 66. The valve 60 is fluidly coupled to the cavity 26 with a fluid passage or conduit (not shown) that extends through the wall. A seal 68, such as an o-ring, may be located between the valve 60 and the sample body 22 to maintain a fluid-tight seal around the valve.

The valve 60 can be opened and closed with an actuator 70 to either permit or prevent fluid passage to and from the sample cavity. In one embodiment, the sample holder employs a syringe valve that can be used in conjunction with a syringe to evacuate the sample cavity and create a vacuum therein by drawing fluid from the sample cavity through the valve using the syringe. In one embodiment, the sample holder employs a MININERT syringe valve, product no. 654051, which is configured for use with a luer-tip syringe. However, it is to be understood that the sample holder may employ any suitable valve arrangement as would be apparent to one of skill in the art.

In some applications, it may be desirable to securely mount a sample in the cavity. In one illustrative embodiment shown in FIGS. 1-2, the sample holder 20 includes an adjustable clamp 72 for securing a sample within the sample cavity 26. The clamp 72 may include a pair of opposed jaws 74, 76 that are adjustable relative to each other vary the distance therebetween for receiving and clamping the sample. In the illustrative embodiment, a first jaw 74 is slidably mounted opposite to a second jaw 76 that is non-movably fixed within the sample cavity. The clamp is adjusted by sliding the first jaw toward and away from the second jaw to vary the spacing therebetween.

Figure 8:
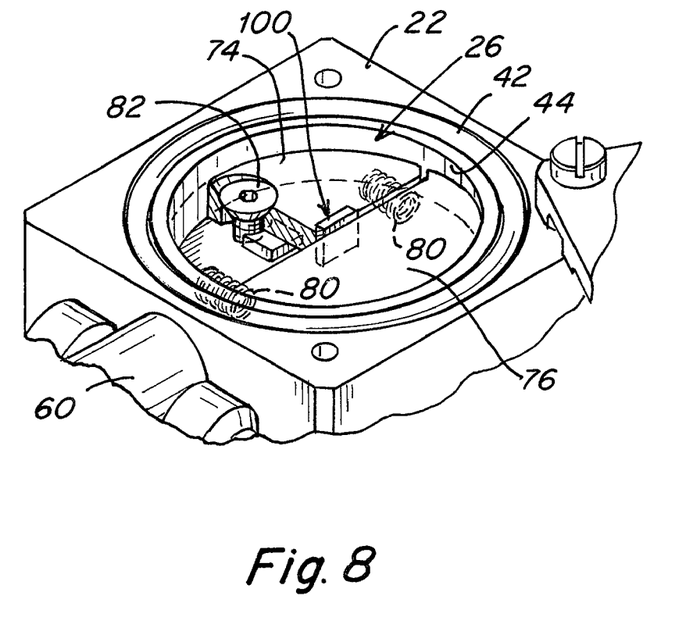
FIG. 8 is an enlarged perspective view of the sample cavity of the hermetic sample holder of FIG. 1 with a clamp and adjuster according to one illustrative embodiment with a first jaw of the clamp shown in phantom to illustrate the clamp and adjuster arrangement.
Figure 9:
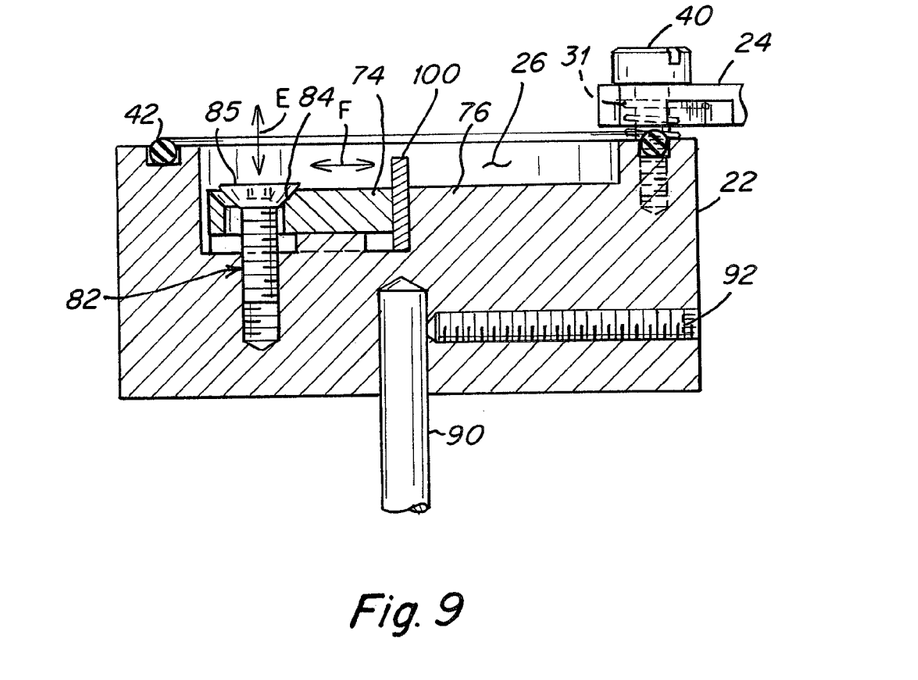
FIG. 9 is a cross-sectional view taken along section line 9-9 of FIG. 2 illustrating the clamp and adjuster arrangement of FIG. 8.

The clamp 72 may include one or more adjustment features to adjust and maintain the clamping jaws in a desired position to secure the sample. In one illustrative embodiment as shown in FIGS. 8-9, the clamp 72 includes an adjuster 78 that is configured to move the first jaw 74 toward and away from the second jaw 76 to vary the distance therebetween for securing and releasing the sample. The adjuster 78 is also configured to maintain the first jaw in a desired position relative to the second jaw.

The adjuster 78 may include a pair of springs 80, such as compression springs, that are located between and exert a force for driving the jaws apart. A wedge arrangement may be provided to drive the first jaw toward and maintain the first jaw in a desired position relative to the second jaw.

The wedge arrangement may include a fastener 82 with a cam surface that cooperates with a corresponding cam surface 84 on the first jaw 74. In one illustrative embodiment as shown in FIGS. 8-9, the fastener 82 includes a flat head screw that engages with the cam surface 84 on the first jaw. Adjusting the height (direction E) of the fastener 82 results in the underside of the screw head 85, which provides a cam surface, interacting with the cam surface 84 on the first jaw 74 in a manner that results in adjusting the position (direction F) of the first jaw 74 relative to the second jaw 76.

As the height of the screw is lowered, the screw head 85 exerts a force on the cam surface 84 of the first jaw 74 that drives the first jaw toward the second jaw 76 to clamp a sample therebetween. Conversely, as the height of the screw is raised, the screw head 85 is similarly raised which allows the first jaw 74 to be driven away from the second jaw 76 by the springs 80 to release a sample from the clamp.

The adjustable clamp 72 may be configured to hold the sample at a desired angle relative to the instrumentation. In one illustrative embodiment as shown in FIGS. 8-9, the clamp 72 is configured to hold a sample 100 on edge at an angle of approximately 90° relative to the upper surface of the clamp. This arrangement may be particularly suited for conducting analysis of the sample cross-section. Rather than holding the sample on edge between the jaws of the clamp, it is to be appreciated that a sample may be mounted in a planar orientation to the upper surface of the clamp using a suitable adhesive. If desired, the clamp may be configured to adjust the angle at which a sample is secured between the jaws relative to the instrumentation.

In one illustrative embodiment, the clamp 72 has an adjustability of approximately 0.8 mm between the jaws to receive and secure samples of varying thicknesses. The clamp may employ compression springs 80 having a spring constant of approximately 1.3 lb/in. However, it is to be understood the sample holder may employ any suitable clamp arrangement as would be apparent to one of skill in the art.

It may be desirable to configure the sample holder so that it can be mounted to the analysis instrument. In one illustrative embodiment shown in FIGS. 1 and 3, the sample holder 20 includes a mounting pin 90 that extends from the bottom of the holder body 22. The pin 90 is configured to be inserted into a corresponding hole or recess provided on the mounting platform of the instrument. The pin 90 may be removably secured to the holder body 22 with a fastener 92, such as a set screw, so that the pin may be removed for instruments having different mounting arrangements.

The sample holder components may be fabricated from various materials suitable for a particular application as would be apparent to one of skill in the art. In one embodiment, the sample holder is manufactured from an aluminum alloy, such as 6061. For applications involving reactive gases, the holder may be made from polytetrafluoroethylene (PTFE), such as TEFLON, in conjunction various metals, graphite, beryllium or other conductive materials for the components that will be adjacent the sample. If desired, the interior of the sample holder may be coated with materials suitable for a particular application. For example, the interior may be coated with carbon and/or other lower atomic number materials for improving capabilities for energy-dispersive X-ray analysis (EDS) by reducing interference with X-rays generated by specimens under study.

It may be desirable to provide a Faraday cup with the sample holder for quantitative X-ray microanalysis. The Faraday cup may include a hollow cylinder having a diameter of about 1-2 mm with a closed end having an entrance aperture with a diameter of about 25-100 µm. As one of ordinary skill in the art would understand, this allows the backscattered and secondary electrons generated by the incident beam to escape from the Faraday cup. The incident beam current will be equal to the current flowing to ground through the Faraday cup, which can be measured with a DC picoampermeter.

The sample holder may include various features to facilitate particular experiments or sample analyses. For heated-stage experiments, the sample holder may include a heater that is located below the sample mount, such as the clamp, within the holder cavity. If desired, the sample holder may include a pair of feed-through electrical connectors for electrochemical experiments (such as galvanostatic and potentiodynamic cycling, pulsing and impedance techniques) utilizing the test instrument connectors to apply voltage and/or current to the sample holder. If desired, a quartz window (not shown) may be incorporated into the holder cover 24 for optical microscopy examination in situ of sealed and/or processed samples. Other features may also be incorporated in the sample holder as would be apparent to one of skill in the art.

As described above, the sample holder is configured to automatically open when the holder is placed in a test instrument that operates under vacuum. In some applications, such as analyzing very reactive samples or samples that need to be retained in pristine condition for further analysis, it may be desirable to automatically reclose the cover under vacuum prior to removal of the holder from an otherwise inaccessible test chamber of the instrument. In doing so, it may be possible to utilize the vacuum of the test instrument to reseal the holder when the vacuum within the test instrument is released after the cover is closed.

It is to be appreciated that various arrangements may be implemented with the sample holder to remotely close the cover, if desired. Several examples include, but are not limited to, memory wires (which may be operated by battery located in a compartment below the sample), a mechanical winding mechanism of set time, electromagnets and electromechanical manipulators which may use an SEM's feed-through connectors for control outside the test chamber. Another non-limiting example includes a 90° electromechanical device powered with DC voltage that is employed with a solenoid to open and close the cover. The arrangement may employ a 90° clamp that rises and lowers as it swings open and closed to thereby raise and lower the cover relative to the holder body.

Because the sample holder is hermetically sealed, it may be desirable to provide an additional port (not shown) that can be utilized for controlled environment experiments. For example, the port may be used for introducing reactive gases, such as methane, nitrogen, carbon dioxide and carbon monoxide, into the holder cavity. The port may also allow for the withdrawal of a gas sample from the holder cavity for analysis, such as by chromatographic separation and thermal conductivity or flame ionization, mass spectrometry detection or even Fourier Transform Infrared Spectroscopy (FTIR) analysis. The port may be located on a side of the holder body opposite the valve. Although a port may be desirable, it is to be appreciated that the valve 60 may be used to introduce and/or remove gases to and from the holder cavity, if desired.

As indicated above, the sample holder may be used to transport a sample to an instrument for microanalysis. One illustrative embodiment of a procedure for using the sample holder is described below in conjunction with FIGS. 4 and 10-11.

Figure 10:
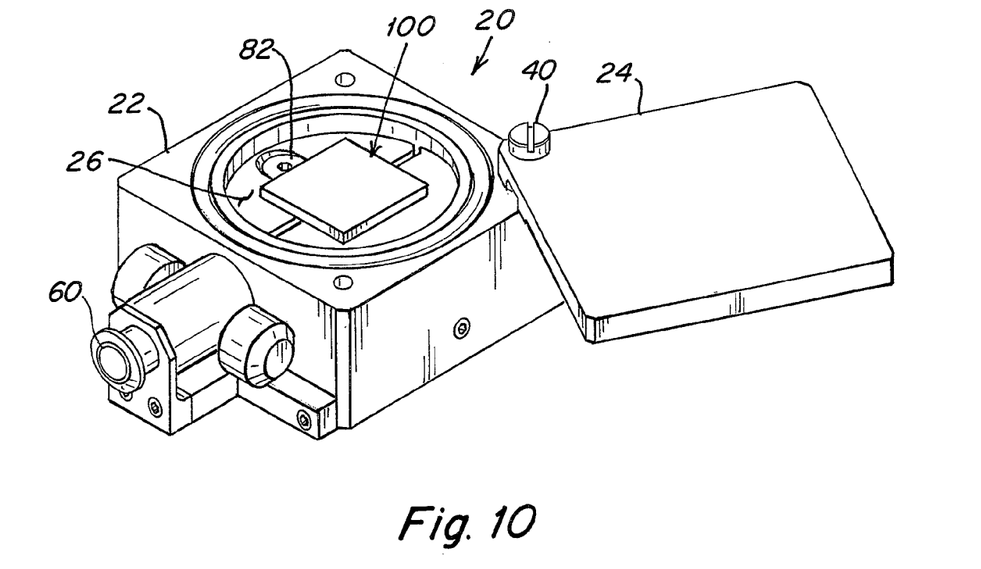
FIG. 10 is a perspective view of the sample holder of FIG. 1 with a sample mounted in a horizontal orientation to the upper surface of the clamp.

With the cover of the sample holder in its open position as shown in FIG. 10, a sample 100 is placed in the sample chamber or cavity 26 of the holder. This may occur within a controlled atmosphere environment, such as a glove box.

Figure 11:
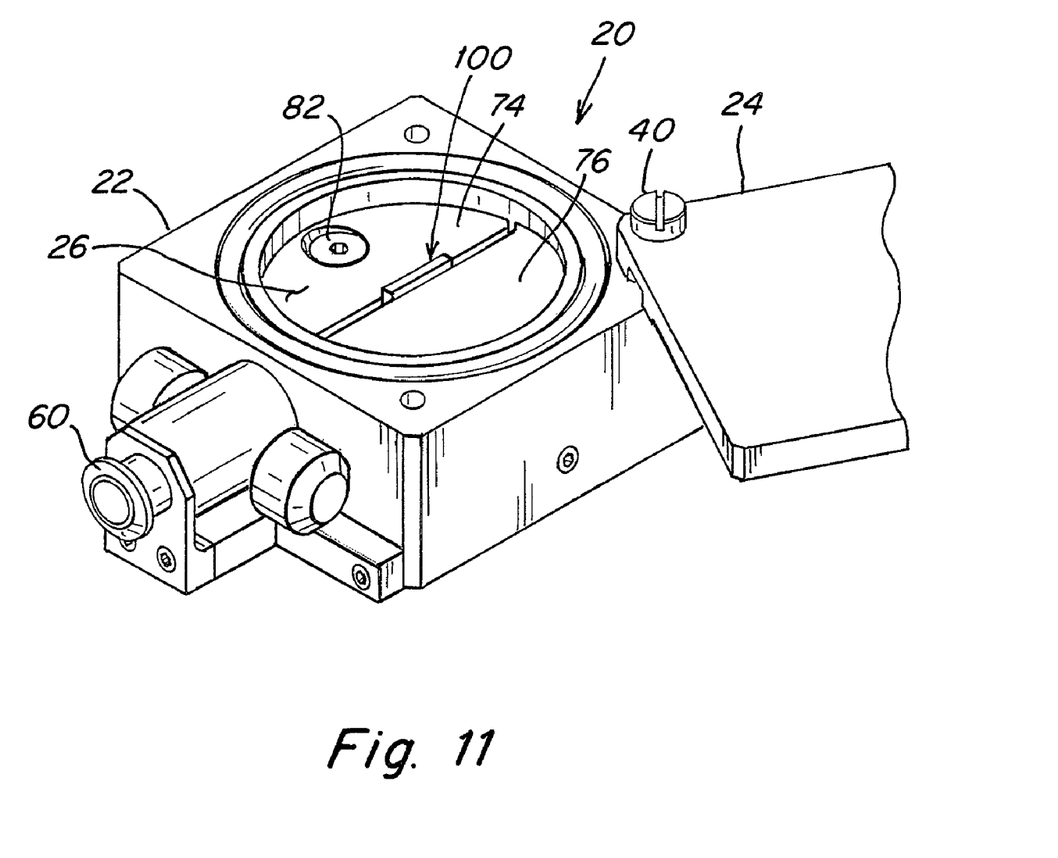
FIG. 11 is a perspective view of the sample holder of FIG. 1 with a sample mounted in a vertical orientation between the jaws of clamp.

As shown in FIG. 10, the sample 100 may be secured to the upper surface of the clamp in a horizontal orientation with a suitable adhesive material or tape. Alternatively, as shown in FIG. 11, the sample 100 may be secured in a vertical orientation with the clamp for conducting analyses of the material cross-section.

Figure 4:
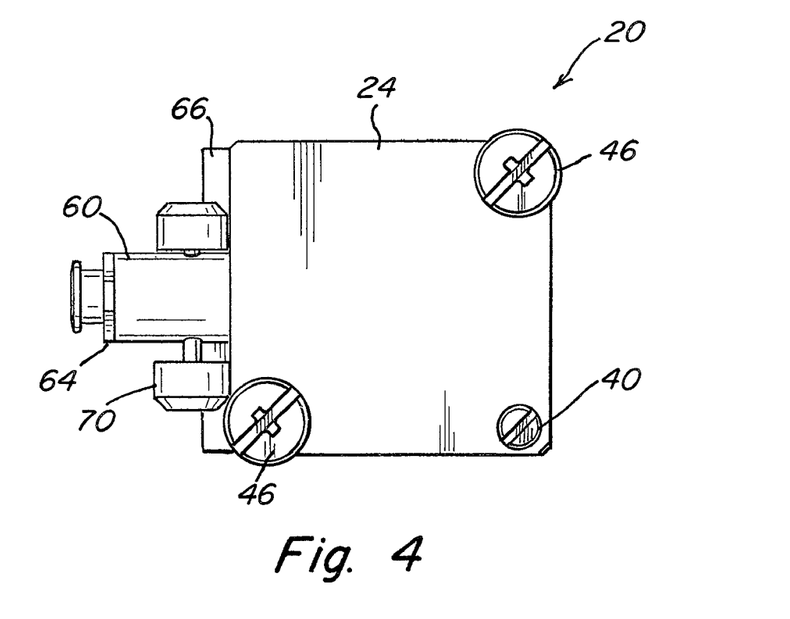
FIG. 4 is a top plan view of the hermetic sample holder of FIG. 1 shown in the closed position.

With the sample secured in the cavity, the cover 24 is placed in its closed position over the cavity, as shown in FIG. 4. As indicated above, the cover may be pivoted or rotated to the closed position against a biasing force generated by a spring 31 that acts to urge the cover to the open position. The cover may be temporarily secured in the closed position with a fastener 46.

With the cover held in its closed position, the sample holder 20 is hermetically sealed with the cover 24 by reducing the pressure of the cavity 26 to a predetermined pressure that is less than the ambient pressure of the controlled atmosphere environment. The pressure differential created in the cavity draws the cover 24 into sealing engagement against the holder body 22 and compresses the seal 42 between the cover and the body. If an interlock is employed, such as shown in FIGS. 6-7B for example, the differential pressure may also cause the interlock to engage and further secure the cover in its closed position against the biasing force of the spring. It is to be appreciated that temporarily securing the cover to the holder body prior to reducing the pressure of the cavity may initially compress the seal and/or engage the interlock.

The pressure of the sample cavity 26 may be reduced by directly evacuating the cavity through a valve 60 provided on the holder body. In one embodiment, the cavity is evacuated using a syringe barrel that is coupled to the valve. The syringe may have a capacity of 2 cc or greater. This arrangement allows the cavity to be evacuated to reduce its pressure independent of adjusting the ambient pressure of the controlled atmosphere environment.

When the cavity has been evacuated sufficiently to create the desired pressure differential for sealing the cover 24 against the holder body 22, the valve 60 may be closed with an actuator 70 to maintain the hermetic seal. The syringe may then be decoupled from the valve.

In one illustrative embodiment, the cavity may have a volume of approximately 1.4 ml. The atmosphere within the cavity may be expanded approximately 15 ml resulting in a negative pressure differential of approximately 13 psi. However, it is to be understood that the sample holder may be configured with a cavity having any desired volume that can be expanded to create a desired pressure differential as would be apparent to one of skill.

Once hermetically sealed, the sample holder 20 can be transported from the controlled atmosphere environment to an instrument analyzer chamber. The sealed holder protects the sample from potential contamination during its transport to the analyzer chamber. Either prior to transport or placement in the analyzer chamber, any fastener 46 temporary securing the cover 24 to the holder body 22 may be unfastened. The cover is maintained in its closed position by the pressure differential between the cavity and the external atmosphere.

After the sample holder is mounted in the analyzer chamber and the chamber is sealed, the cover 24 is released to expose the sample 100 to the atmosphere of the analyzer chamber. This may be achieved by reducing the pressure of the analyzer chamber to a pressure that approaches or is less than the pressure of the sample cavity.

As the analyzer chamber pressure approaches and then falls below the sample cavity pressure, the external pressure on the cover will begin to equalize with and then fall below the internal cavity pressure of the holder. The seal 42 between the cover 24 and the holder body 22 will begin to decompress, thereby allowing the cover to rise slightly from the holder body. If employed, the interlock 50 between the cover and the holder body will disengage. Once the biasing force of the spring 31 exceeds the differential pressure forces, the cover will open to expose the sample.

It may be desirable to compare and analyze protected and unprotected samples during the same session of sample analysis. In one embodiment, a portion of the sample may be sealed in the sample cavity in a manner as described above, while another portion of the sample may be mounted to the external surface of the cover.

The embodiments of the hermetic sample holder described above is particularly suited for SEM analysis with major types of SEMs including, but not limited to, field-emission SEMs (FESEMs), variable pressure SEMs (VP-SEMs), environmental SEMs (ESEMs) and other microanalyses. It is also to be appreciated that the sample holder may be modified, as desired, for these and other microanalysis uses as would be apparent to one of ordinary skill in the art.

It should be understood that the foregoing description of various embodiments of aspects of the invention are intended merely to be illustrative thereof and that other embodiments, modifications, and equivalents of the invention are within the scope of the invention recited in the claims appended hereto.

What is claimed is:

1. A hermetic sample holder for use in performing microanalysis of a sample, the sample holder comprising:
   a sample holder body with a sample cavity to receive the sample that is to be subjected to microanalysis; and
   a cover including a sealing surface that cooperates with the sample holder body to seal the sample cavity, the cover being pivotally mounted to the sample holder body about a pivot axis that is perpendicular to the sealing surface, the cover being pivotal between an open position to allow access to the sample cavity and a closed position to hermetically seal the sample cavity, the cover to be secured in the closed position and released from the closed position at least in part by a pressure differential between an internal pressure within the sample cavity and an ambient pressure outside the sample cavity.

2. The hermetic sample holder according to claim 1, wherein the cover is biased toward the open position.

3. The hermetic sample holder according to claim 2, further comprising a spring to bias the cover toward the open position, wherein the spring is located about the pivot axis.

4. The hermetic sample holder according to claim 1, wherein the cover is movable toward and away from the sample holder body in a direction along the pivot axis.

5. The hermetic sample holder according to claim 1, further comprising a valve in fluid communication with the sample cavity to allow direct evacuation of the sample cavity to create a pressure differential between the sample cavity and the ambient pressure.

6. The hermetic sample holder according to claim 1, further comprising an adjustable clamp located in the sample cavity to secure the sample.

7. The hermetic sample holder according to claim 1, further comprising an interlock between the cover and the sample holder body to secure the cover in the closed position, the interlock configured to secure and release the cover based on the differential pressure between the internal and ambient pressures.

8. The hermetic sample holder according to claim 1, further comprising a seal to hermetically seal the cover to the sample holder when the cover is placed in the closed position and a pressure differential is created between the internal and ambient pressures.

9. A hermetic sample holder for use in performing microanalysis of a sample, the sample holder comprising:
   a sample holder body with a sample cavity to receive the sample that is to be subjected to microanalysis; and
   a cover pivotally mounted to the sample holder body, the cover being pivotal about an axis between an open position to allow access to the sample cavity and a closed position to hermetically seal the sample cavity, the cover being movable in a direction along the axis toward and away from the sample holder body, the cover to be secured in the closed position and released from the closed position at least in part by a pressure differential between an internal pressure within the sample cavity and an ambient pressure outside the sample cavity.

10. The hermetic sample holder according to claim 9, wherein the cover is biased toward the open position.

11. The hermetic sample holder according to claim 9, wherein the cover includes a sealing surface to seal the cover with the sample holder body, the pivot axis being oriented perpendicular to the sealing surface.

12. The hermetic sample holder according to claim 9, further comprising a valve in fluid communication with the sample cavity to allow direct evacuation of the sample cavity to create a pressure differential between the sample cavity and the ambient pressure.

13. The hermetic sample holder according to claim 9, further comprising an adjustable clamp located in the sample cavity to secure the sample.

14. The hermetic sample holder according to claim 9, further comprising an interlock between the cover and the sample holder body to secure the cover in the closed position, the interlock configured to secure and release the cover based on the differential pressure between the internal and ambient pressures.

15. The hermetic sample holder according to claim 9, further comprising a seal to hermetically seal the cover to the sample holder when the cover is placed in the closed position and a pressure differential is created between the internal and ambient pressures.

\* \* \* \* \*